United States Patent [19]
Westphal et al.

[11] 3,961,936
[45] June 8, 1976

[54] HERBICIDAL AGENTS

[75] Inventors: Kurt Westphal, Wuppertal-Vohwinkel; Werner Meiser, Wuppertal-Elberfeld; Ludwig Eue, Cologne-Stammheim; Helmuth Hack, Cologne-Buchheim, all of Germany

[73] Assignee: Bayer Aktiengesellschaft, Leverkusen, Germany

[22] Filed: Apr. 12, 1967

[21] Appl. No.: 630,225

[30] Foreign Application Priority Data
Apr. 16, 1966 Germany................................ 48954

[52] U.S. Cl.......................................... 71/93; 71/73; 71/74; 71/75; 71/88; 71/90; 71/92; 260/240 A; 260/240 G; 260/247.1 M; 260/248 AS; 260/249.5; 260/247.7 R; 260/247.7 T
[51] Int. Cl.²........................................... A01N 9/22
[58] Field of Search................................. 71/93, 88

[56] References Cited
UNITED STATES PATENTS

| | | |
|---|---|---|
| 3,235,358 | 2/1966 | Soboczenski ........................... 71/93 |
| 3,322,526 | 5/1967 | Loux........................................ 71/93 |
| 3,337,550 | 8/1967 | Yates et al.............................. 71/93 |
| 3,905,801 | 9/1975 | Fawzi...................................... 71/93 |

OTHER PUBLICATIONS

Dornow et al., "Uber 1,2,4–Triazine I. etc.," (1964) Chem. Ber. 97 pp. 2173–2178 (1964).

*Primary Examiner*—Glennon H. Hollrah
*Attorney, Agent, or Firm*—Burgess, Dinklage & Sprung

[57] ABSTRACT

3-[hydrogen-, (unsubstituted and halo, amino, nitro, alkyl, alkanoyl, alkoxy, alkylmercapto, aryloxy and/or aryl-mercapto-substituted) aliphatic-, cycloaliphatic-, araliphatic-, aryl-, or heterocyclic- -substituted oxy, mercapto or amino]4-[amino; mono and di (unsubstituted and cyano, hydroxy and/or halo-substituted) alkyl- and/or alkanoyl-amino; N-heterocyclic; or N-(unsubstituted and aryl, haloaryl, alkoxyaryl, nitroaryl and/or heterocyclic- substituted) alkylidene or cycloalkylidene]-6-[(unsubstituted and halo, nitro, carbo lower alkoxy, alkyl, alkoxy, alkylmercapto, aralkylmercapto, aryloxy and/or arylmercapto-substituted) aliphatic, cycloaliphatic, araliphatic, aryl, or heterocyclic]-1,2,4-triazine-5-ones, which possess herbicidal properties, and which may be produced by conventional methods.

4 Claims, No Drawings

HERBICIDAL AGENTS

The present invention relates to and has for its objects the provision for particular substituted 4-amino-1,2,4-triazine-5-ones, some of which are known, which possess valuable, especially selective, herbicidal properties, active compositions in the form of mixtures thereof wich solid and liquid dispersible carrier vehicles, and methods for their preparation and use, especially for combatting weeds, undesired plants, and the like; with other and further objects of this invention becoming apparent from a study of the within specification and accompanying examples.

It is known that 1,3,5-triazines can be used for the control of weeds (see Belgian Pat. No. 540,590). In this group of active compounds, 2,6-di-(ethylamino)-4-chloro-1,3,5-triazine (A) has attained a considerable practical significance.

It has now been found, in accordance with the present invention, that the particular 4-amino-1,2,4-triazine-5-ones having the formula

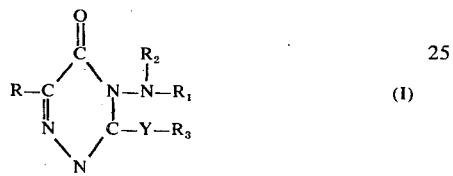

in which
  R is selected from the group consisting of aliphatic having 1–18 carbon atoms, cycloaliphatic having 5–8 ring carbon atoms, araliphatic having 6–10 ring carbon atoms in the corresponding aryl moiety and 1–4 carbon atoms in the aliphatic moiety, aryl having 6–10 ring carbon atoms, heterocyclic having 5–6 ring members with at least one hetero linking atom selected from the group consisting of O, N, S and mixtures of such hetero atoms, and such aliphatic, cycloaliphatic, araliphatic, aryl and heterocyclic which is substituted with a substituent selected from the group consisting of halo, nito, carbo lower alkoxy, lower alkyl, lower alkoxy, aryl-lower alkylmercapto having 6–10 ring carbon atoms in the aryl moiety, lower alkylmercapto, arylmercapto having 6–10 ring carbon atoms, aryloxy having 6–10 ring carbon atoms, and mixtures of such substituents;
  $R_1$ and $R_2$ each respectively is selected from the group consisting of hydrogen, alkyl having 1–12 carbon atoms, alkanoyl having 1–6 carbon atoms, and such alkyl and alkanoyl which is substituted with a substituent selected from the group consisting of cyano, hydroxy, halo, and mixtures of such substituents, with the proviso that $R_1$ and $R_2$ when taken together represent alkylidene having 1–6 carbon atoms, cycloalkylidene having 5–8 ring carbon atoms, and such alkylidene and cycloalkylidene which is substituted with a substituent selected from the group consisting of aryl having 6–10 ring carbon atoms, haloaryl having 6–10 ring carbon atoms, lower alkoxy aryl having 6–10 ring carbon atoms in the aryl moiety, nitroaryl having 6–10 ring carbon atoms, heterocyclic having 5–6 ring members with at least one hetero linking atom selected from the group consisting of O, N, S and mixtures of such hetero atoms, and mixtures of such substituents;
  Y is selected from the group consisting of O, S and

and
  $R_3$ and $R_4$ each respectively is selected from the group consisting of hydrogen, aliphatic having 1–18 carbon atoms, cycloaliphatic having 5–8 ring carbon atoms, araliphatic having 6–10 ring carbon atoms in the corresponding aryl moiety and 1–4 carton atoms in the aliphatic moiety, aryl having 6–10 ring carbon atoms, and such aliphatic, cycloaliphatic, araliphatic and aryl which is substituted with a substituent selected from the group consisting of halo, amino, lower alkyl substituted amino, nitro, lower alkyl, lower alkoxy, aryloxy having 6–10 ring carbon atoms, and mixtures of such substituents, with the proviso that $R_3$ and $R_4$ when taken together with the adjacent N atom represent heterocyclic having 5–6 ring members with at least one hetero linking atom selected from the group consisting of O, N, S and mixtures of such hetero atoms; and with the further proviso that when Y is O then $R_3$ may also be lower alkanoyl; exhibit strong herbicidal properties.

It is very surprising that the particular active compounds usable according to the present invention not only show a stronger herbicidal activity than the known triazines in pre-emergence application but also show a good herbicidal activity when used according to the post-emergence method. Apart from this, the instant compounds also show marked selective herbicidal properties (see Examples 1 and 2 hereinbelow).

Some of the 1,2,4-triazine-5-ones usable according to the present invention are already known from the literature.

The following compounds are new: 1,2,4-triazine-5-ones of the above formula (I) wherein correspondingly:
a.
  R, $R_1$, $R_2$ and $R_3$ are the same as defined above, and
  Y is oxygen, provided that $R_3$ may also be alkanoyl; or
b.
  R is aliphatic hydrocarbon having at least two, or at least three, or at least four, or at least five, or at least six, or more, carbon atoms, cycloaliphatic hydrocarbon, araliphatic hydrocarbon or heterocyclic which, in each case, may be substituted with one or more halogen, nitro, alkyl, alkoxy, carboalkoxy, aralkylmercapto, alkylmercapto, aryloxy and/or arylmercapto, or R is aryl substituted with one or more halogen, nitro, alkyl, alkoxy, carboalkoxy, aralkylmercapto, alkylmercapto, aryloxy and/or arylmercapto,
  $R_1$, $R_2$ and $R_3$ are the same as defined above, and
  Y is sulfur; or
c.
  R, $R_1$ and $R_2$ are the same as defined above,
  $R_3$ is aliphatic hydrocarbon having at least two, or at least three, or at least four, or at least five, or at least six, or more, carbon atoms, cycloaliphatic hydrocarbon, araliphatic hydrocarbon, aryl or heterocyclic which, in each case, may be substituted with one or more halo, amino, nitro, alkyl, alkoxy, carboalkoxy, aralkylmercapto, alkylmercapto, aryloxy and/or arylmercapto, and Y is sulfur; or d.

R and $R_3$ are the same as defined above, $R_1$ and $R_2$ each individually is alkyl which may be substituted with one or more cyano, hydroxy and/or halogen, or $R_1$ and $R_2$, together with the adjacent nitrogen atom, represent heterocyclic, or $R_1$ and $R_2$ taken jointly represent alkylidene which may be substituted with one or more aryl halide, alkoxyaryl, nitroaryl and/or heterocyclic or represent alkylidene having at least two, or at least three, or at least four, or at least five, or at least six, or more, carbon atoms which is substituted with aryl, or represent cycloalkylidene, and Y is sulfur; or e.

R is aliphatic hydrocarbon having at least two, or at least three, or at least four, or at least five, or at least six, or more, carbon atoms, cycloaliphatic hydrocarbon, araliphatic hydrocarbon, or heterocyclic which, in each case, may be substituted with one or more halogen, nitro, alkyl, alkoxy, carboalkoxy, aralkylmercapto, alkylmercapto, aryloxy and/or arylmercapto, or R is aryl substituted with one or more halogen, nitro, alkyl, alkoxy, carboalkoxy, aralkylmercapto, alkylmercapto, aryloxy and/or arylmercapto, $R_1$, $R_2$, $R_3$ and $R_4$ are the same as defined above, and Y is $=NR_4$; or f.

R, $R_3$ and $R_4$ are the same as defined above, $R_1$ and $R_2$ each individually is alkyl or acyl, i.e., alkanoyl, which may be substituted with one or more cyano, hydroxy and/or halogen, or $R_1$ and $R_2$, together with the adjacent nitrogen atom, represent heterocyclic, or $R_1$ and $R_2$ taken jointly represent alkylidene which may be substituted with one or more aryl, aryl halide, alkoxyaryl, nitroaryl and/or heterocyclic, and Y is $=NR_4$; or g.

R, $R_1$ and $R_2$ are the same as defined above, $R_3$ is hydrogen and $R_4$ is unsubstituted aliphatic hydrocarbon having up to three carbon atoms, substituted aliphatic hydrocarbon, substituted or unsubstituted cycloaliphatic hydrocarbon or substituted aryl, or $R_3$ and $R_4$ each individually is substituted or unsubstituted aliphatic hydrocarbon, cycloaliphatic hydrocarbon or aryl, or $R_3$ and $R_4$, together with the adjacent nitrogen, represent oxygenfree heterocyclic which may be substituted with one or more halo, amino, nitro, alkyl, alkoxy, alkylmercapto, aryloxy, carboalkoxy, aralkylmercapto, and/or arylmercapto, and Y is $=NR_4$.

The instant new triazinones can be prepared according to the customary methods in the same manner as the known triazinones [see for example Berichte 97, 2173–2178 (1964)].

Advantageously, the instant triazinones influence plant growth and can be used as defoliants, desiccants or herbicides and in particular as weed-killers.

By defoliants and desiccants are meant the customary harvest auxiliaries which are used for removing the leaves from and for drying out the green portions of plants before bringing in the harvest.

By weeds are meant in the widest sense all plants which grow in places where they are undesired.

The instant triazinones can be used as total herbicides for the destruction of weeds, and also as selective herbicides for the destruction of weeds in connection with the cultivation of specific agricultural crops. Whether the instant triazinones act as total herbicides or as selective herbicides depends largely on the concentration thereof which is used as the artisan aware of the present invention will appreciate. Examples of crops for which the triazinones of the instant invention are suitable are cereals (such as oats, barley, rice, maize and in particular wheat), cotton, carrots, snap beans, peas, potatoes, beets, and the like.

As weeds which can be destroyed in accordance with the present invention, there may be mentioned as illustrative examples: dicotyledons, such as mustard (Sinapis), cress (Lepidium), cleaver (Galium), common chickweed (Stellaria), camomile (Matricaria), smallflower Galinsoga (Galinsoga), fathen (Chenopodium), burning nettle (Urtica), groundsel (Senecio); monocotyledons, such as timothy (Phleum), meadow grass (Poa), fescue grass (Festuca), goosegrass (Eleusine), foxtail (Setaria), ryegrass (Lolium), brome grass (Bromus), barnyard grass (Echinochloa), and the like.

The active compounds according to the instant invention can be utilized, if desired, in the form of the usual formulations or compositions with dispersible carrier vehicles, such as solutions, emulsions, suspensions, emulsifiable concentrates, spray powders, pastes, soluble powders, dusting agents, granulates, etc. These are prepared in known manner, for instance by extending the active agents with dispersible liquid diluent carriers and/or dispersible solid carriers optionally with the use of carrier vehicle assistants, e.g., surfaceactive agents, including emulsifying agents and/or dispersing agents, whereby, for example, in the case where water is used as diluent, organic solvents may be added as auxiliary solvents (see Agricultural Chemicals, March 1960, pp. 35–38). The following may be chiefly considered for use as carrier vehicles for this purpose: dispersible liquid diluent carriers, such as aromatic hydrocarbons (for instance, benzene, toluene, xylene, etc.), halogenated, especially chlorinated, aromatic hydrocarbons (for instance, chlorobenzenes), paraffins (for instance, petroleum fractions), chlorinated aliphatic hydrocarbons (for instance, methylene chloride, etc.), alcohols (for instance, methanol, ethanol, propanol, butanol, etc.), ethers, etheralcohols (for instance, glycol monomethyl ether, etc.), amines (for instance, ethanolamine, etc.), amides (for instance dimethyl formamide, etc.), sulfoxides (for instance, dimethyl sulfoxide, etc.), ketones (for instance, acetone, etc.), and water; as well as dispersible finely divided solid carriers, such as ground natural minerals (for instance, kaolins, alumina, silica, chalk, i.e., calcium carbonate, talc, kieselguhr, etc.), and ground synthetic minerals (for instance, highly dispersed silicic acid, silicates, e.g., alkali silicates, etc.); whereas the following may be chiefly considered for use as carrier vehicle assistants, e.g., surface-active agents, for this purpose: emulsifying agents, such as nonionic and anionic emulsifying agents (for instance, polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and dispersing agents, such as lignin, sulfite waste liquors, methyl cellulose, etc.

As will be appreciated by the artisan, the active compounds according to the instant invention may be present in such formulations or compositions in the form of mixtures with one another and with other known active substances such as for example known herbicides including ureas, other triazines, uracils, aminotriazole, phenoxy carboxylic acids, benzoic acid, picolinic acid, and the like, if desired.

The substances according to the invention may be employed, therefore, by themselves as the artisan will appreciate, in the form of their compositions with solid or liquid dispersible carrier vehicles or other known compatible active agents, or in the form of particular dosage preparations for specific application made therefrom, such as solutions, emulsions, suspensions, powders, pastes, and granulates which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.001 and 1.0%, preferably 0.005 and 0.5%, by weight of the mixture. Thus, the present invention contemplates over-all compositions which comprise mixtures of a dispersible carrier vehicle such as a dispersible carrier solid, or a dispersible carrier liquid preferably including a carrier vehicle assistant, e.g., a surface-active agent, such as an emulsifying agent and/or a dispersing agent, and an amount of the active compound which is effective for the purpose in question and which is generally between about 0.001 and 95% by weight of the mixture. Specifically, the active compound may be applied to a surface area, such as in pre-emergence use, in concentrations substantially between about 0.5 and 20 kg per hectare, preferably between about 1 and 10 kg per hectare, although it will be appreciated that in connection with the pre-emergence use of the instant compounds, as well as the post-emergence use thereof, the concentration may be varied within a fairly wide range. However, generally the post-emergence range of concentration will be between about 0.001 and 95%, preferably between about 0.005 and 95%, by weight of the mixture as aforesaid, while the pre-emergence range will be between about 0.5 and 20, preferably between about 1 and 10, kg per hectare, as aforesaid.

Furthermore, the present invention contemplates methods of selectively controlling or combatting undesired plants, e.g., weeds and the like, which comprise applying to at least one of (a) such weeds and (b) their habitat, a herbicidally effective amount of the particular active compound of the invention alone or together with a carrier vehicle as noted above. The instant formulations or compositions are applied in the usual manner, for example, by spraying, atomizing, scattering, dusting, watering, sprinkling, dispersing, and the like, whether for pre-emergence application to the soil or post-emergence application to the weeds.

The following Examples are given for the purpose of illustrating, without limiting, the utility of the instant invention.

EXAMPLE 1

Pre-emergence test

Solvent: 5 parts by weight acetone
Emulsifier: 1 part by weight benzyloxypolyglycol ether To produce a suitable preparation of the particular active compound, 1 part by weight of such active compound is mixed with the stated amount of solvent, the stated amount of emulsifier is then added and the resulting concentrate is thereafter diluted with water to the desired final concentration.

Seeds of the test plants are sown in normal soil and, after 24 hours, watered with the preparation of the given active compound. It is expedient to keep constant the amount of water per unit area. The concentration of the particular active compound in the preparation is of no importance, only the amount of active compound applied per unit area being decisive. After three weeks, the degree of damage to the test plants is determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The particular active compounds, the amounts applied and the results obtained can be seen from the following Table 1:

Table 1

| Active compound | Active compound used in kg/hectare | Oats | Wheat | Cotton | Sinapis | Chenopodium | Galinsoga | Echinochloa | Avena fatua |
|---|---|---|---|---|---|---|---|---|---|
| (A) 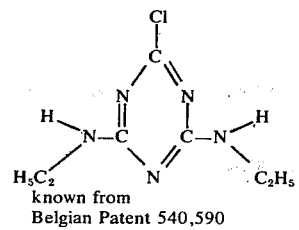 known from Belgian Patent 540,590 | 5 | 4 | 4 | 5 | 5 | 5 | 5 | 3–4 | 5 |
|  | 2.5 | 4 | 3 | 4 | 5 | 5 | 5 | 3 | 4 |
|  | 1.25 | 3 | 2 | 3 | 5 | 5 | 5 | 2 | 3 |
| (1a) 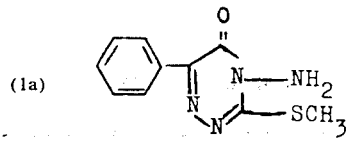 | 5 | 5 | 5 | 3 | 5 | 5 | 5 | 5 | 5 |
|  | 2.5 | 5 | 5 | 1 | 5 | 5 | 5 | 5 | 5 |
|  | 1.25 | 3 | 2 | 0 | 5 | 5 | 5 | 4–5 | 4 |

Table 1-continued

| Active compound | Active compound used in kg/hectare | Pre-emergence test Oats | Wheat | Cotton | Sinapis | Chenopodium | Galinsoga | Echinochloa | Avena fatua |
|---|---|---|---|---|---|---|---|---|---|
| (2) 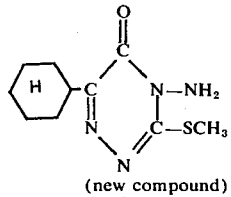 (new compound) | 5 | 5 | 5 | 5 | 5 | 5 | 5 | 5 | |
| | 2.5 | 5 | 5 | 5 | 5 | 5 | 5 | 5 | |
| | 1.25 | 4–5 | 4–5 | 5 | 5 | 5 | 5 | 5 | |
| (3) 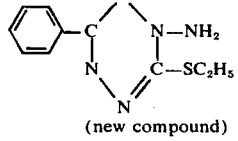 (new compound) | 10 | 3 | 1 | 0 | 5 | 5 | 5 | 5 | |
| | 5 | 2 | 0 | 0 | 5 | 5 | 5 | 4 | |
| | 2.5 | 1 | 0 | 0 | 4 | 5 | 5 | 3 | |

The following instant compounds having the appropriate substituents designated in Table 1A for Formula (I) act in the same way as active compound (1a):

Table 1A

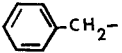

(I)

| | R | $R_1$ | $R_2$ | $R_3$ | $R_4$ | Y | |
|---|---|---|---|---|---|---|---|
| (4) | 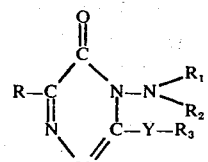 | H | H | —$CH_3$ | | S | new compound |
| (5) |  | H | H | —$CH_3$ | | S | new compound |
| (6) | 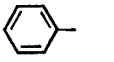 | —CO—$CH_3$ | —$COCH_3$ | —$CH_3$ | | S | new compound |
| (7) | 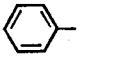 | H | H | —$C_2H_5$ | H | N | new compound |
| (8) | 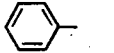 | —$COCH_3$ | H | —$CH_3$ | | S | new compound |
| (9) | 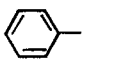 | H | H | —$CH_3$ | H | N | new compound |
| (10) | 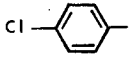 | H | H | —$CH_3$ | H | N | new compound |
| (11) | 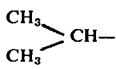 | H | H | —$CH_3$ | | S | new compound |
| (12) | 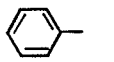 | H | H | —$CH_2$—$CH_2$—$CH_3$ | H | N | new compound |
| (13a) | 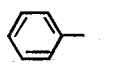 | H | H | —$CH_2$—$CH_2$—O—$CH_2CH_2$— | | N | |

The following instant compounds having the appropriate substituents designated in Table 1B for Formula (I) above act in the same way as active compound (2), which has a pronouncedly total-herbicidal action:

(I) above act in the same way as active compound (3), which exhibits selectively herbicidal action in wheat and cotton:

Table 1B

| | R | R$_1$ | R$_2$ | R$_3$ | R$_4$ | Y | |
|---|---|---|---|---|---|---|---|
| (14) |  | =CH—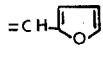 | | —CH$_3$ | | S | new compound |
| (15) | 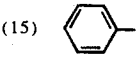 | =CH—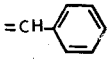 | | —CH$_3$ | | S | new compound |
| (16) | 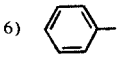 | H | H | —CH$_3$ | —CH$_3$ | N | new compound |
| (17) | 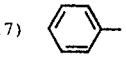 | =C(CH$_3$)$_2$ | | —CH$_3$ | | S | new compound |
| (18) | 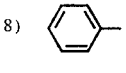 | =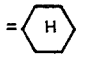 | | —CH$_3$ | | S | new compound |
| (19) | 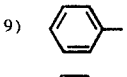 | =CH—CH(CH$_3$)$_2$ | | —CH$_3$ | | S | new compound |
| (20) | 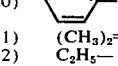 | —CHOH—CCl$_3$ | H | —CH$_3$ | | S | new compound |
| (21) | (CH$_3$)$_2$=CH— | H | H | —CH$_3$ | | S | new compound |
| (22) | C$_2$H$_5$— | H | H | —CH$_3$ | | S | new compound |
| (23) | iso C$_5$H$_{11}$— | H | H | —CH$_3$ | | S | new compound |
| (24) | C$_6$H$_{13}$n— | H | H | —CH$_3$ | | S | new compound |

The following instant compounds having the appropriate substituents designated in Table 1C for Formula Table 1C

| | R | R$_1$ | R$_2$ | R$_3$ | R$_4$ | Y |
|---|---|---|---|---|---|---|
| (25) |  | H | H | —CH$_2$—CH$_2$\<br>          \>CH$_2$<br>—CH$_2$—CH$_2$/ | | N new compound |
| (26) |  | H | H | —CH$_2$—CH=CH$_2$ | H | N new compound |
| (27) |  | =C<CH$_3$<br> | | —CH$_3$ | | S new compound |
| (28) | 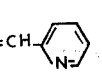 | =CH—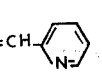 | | —CH$_3$ | | S new compound |

EXAMPLE 2

Post-emergence test

Solvent: 5 parts by weight acetone
Emulsifier: 1 part by weight benzyloxypolyglycol ether To produce a suitable preparation of the particular active compound, 1 part by weight of such active compound is mixed with the stated amount of solvent, the stated amount of emulsifier is then added and the resulting concentrate is thereafter diluted with water to the desired final concentration.

Test plants which have a height of about 5–15 cm. are sprayed with the preparation of the given active compound until just dew moist. After three weeks, the degree of damage to the plants is determined and characterized by the values 0–5, which have the following meaning:

0 no effect
1 a few slightly burnt spots
2 marked damage to leaves
3 some leaves and parts of stalks partially dead
4 plant partially destroyed
5 plant completely dead The particular active compounds, their concentrations and the results obtained can be seen from the following Table 2:

Table 2

| Active | Concentration of active compound % | Wheat | Sinapis | Chenopodium | Stellaria | Daucus | Galinsoga | Echinochloa |
|---|---|---|---|---|---|---|---|---|
| (A') [structure: chlorotriazine with H₅C₂-NH and C₂H₅-NH substituents] (known from Belgian Patent 540,590) | 0.1 | 4 | 5 | 5 | 5 | 3 | 4–5 | 4 |
| | 0.05 | 2 | 5 | 5 | 5 | 1 | 4 | 3 |
| | 0.025 | 1 | 5 | 4 | 5 | 0 | 2 | 2 |
| | 0.01 | 0 | 4 | 3 | 4 | 0 | 1 | 1 |
| (1a') [structure: 6-phenyl-3-methylthio-triazinone with N-NH₂] | 0.1 | 4 | 5 | 5 | 5 | 5 | 5 | 5 |
| | 0.05 | 2 | 5 | 5 | 5 | 5 | 5 | 5 |
| | 0.025 | 1 | 5 | 5 | 5 | 5 | 5 | 5 |
| | 0.01 | 0 | 5 | 5 | 5 | 5 | 5 | 5 |

Table 2'

| Active compound | Concentration of active compound % | Wheat | Carrots | Snap Beans | Sinapis | Chenopodium | Stellaria | Galinsoga | Echinochloa |
|---|---|---|---|---|---|---|---|---|---|
| (21') (CH₃)₂CH—[structure with N—NH₂ and C—SCH₃] (new compound) | 0.05 | 5 | 5 | 5 | 5 | 5 | 5 | 5 | 5 |
| | 0.025 | 5 | 5 | 5 | 5 | 5 | 5 | 5 | 5 |
| | 0.01 | 4–5 | 5 | 5 | 5 | 5 | 5 | 5 | 5 |
| (28') [phenyl-triazinone with N=CH-pyridyl and C-SCH₃] (new compound) | 0.05 | 1 | 5 | 1 | 5 | 5 | 5 | 5 | 5 |
| | 0.025 | 0 | 5 | 0 | 5 | 5 | 5 | 5 | 5 |
| | 0.01 | 0 | 5 | 0 | 5 | 5 | 5 | 4 | 4 |
| (26') [phenyl-triazinone with N—NH₂ and NH—CH₂—CH=CH₂] (new compound) | 0.05 | 0 | 0 | 5 | 5 | 5 | 5 | 5 | 5 |
| | 0.025 | 0 | 0 | 5 | 5 | 5 | 5 | 5 | 4 |
| | 0.01 | 0 | 0 | 4 | 5 | 5 | 4 | 5 | 3 |

The following instant compounds having the appropriate substituents designated in Table 2A for Formula (I) above act in the same way as active compound (1a):

Table 2A

[Structure: R-C=N-N(R1)(N-C(=O))-C(-Y-R3)=N ring with R4]

| | R | R₁ | R₂ | R₃ | R₄ | Y | |
|---|---|---|---|---|---|---|---|
| (29a) | CH₃— | H | H | —CH₃ | | S | |
| (4') | C₆H₅—CH₂— | H | H | —CH₃ | | S | new compound |
| (30) | Cl—C₆H₄—CH₂— | H | H | —CH₃ | | S | new compound |
| (31) | C₆H₅— | H | H | —CH₂—C≡CH | | S | new compound |
| (32) | C₆H₅— | H | H | —CH₂—CH=CH₂ | | S | new compound |
| (7') | C₆H₅— | H | H | —C₂H₅ | H | N | new compound |
| (33) | C₆H₅— | H | H | —CH₃ | | O | new compound |
| (9') | C₆H₅— | H | H | —CH₃ | H | N | new compound |
| (10') | Cl—C₆H₄—CH₂— | H | H | —CH₃ | H | N | new compound |
| (11') | (CH₃)₂CH—CH₂— | H | H | —CH₃ | | S | new compound |
| (34) | CH₃— | H | H | —CH₃ | H | N | new compound |
| (13a') | C₆H₅— | H | H | —CH₂—CH₂—O—CH₂—CH₂— | | N | |

The following instant compounds having the appropriate substituents designated in Table 2B for Formula (I) above act in the same way as active compound (21), which has a pronouncedly total-herbicidal action:

Table 2B

| | R | R₁ | R₂ | R₃ | R₄ | Y | |
|---|---|---|---|---|---|---|---|
| (14') | C₆H₅— | =CH—(furyl) | | —CH₃ | | S | new compound |
| (16') | C₆H₅— | H | H | —CH₃ | —CH₃ | N | new compound |
| (2') | C₆H₁₁— | H | H | —CH₃ | | S | new compound |
| (20') | C₆H₅— | —CHOH—CCl₃ | H | —CH₃ | | S | new compound |
| (23') | iso C₅H₁₁— | H | H | —CH₃ | | S | new compound |

The following instant compounds having the appropriate substituents designated in Table 2C for Formula (I) above act in the same way as active compound (28), which exhibits a pronouncedly selective-herbicidal action in snap beans and wheat:

The harvesting of the beans is quite considerably facilitated in this manner.

The same action is exercised by:
(29a') 3-methylthio-4-amino-6-methyl-1,2,4-triazine-5-one Table 2C

| | R | $R_1$ | $R_2$ | $R_3$ | $R_4$ | Y | |
|---|---|---|---|---|---|---|---|
| (15') | phenyl | | =CH–phenyl | | –CH₃ | S | new compound |
| (27') | phenyl | | =C(CH₃)–phenyl | | –CH₃ | S | new compound |
| (19') | phenyl | | =CH–CH(CH₃)₂ | | –CH₃ | S | new compound |
| (22') | C₂H₅– | H | H | | –CH₃ | S | new compound |
| (24') | C₆H₁₃n- | H | H | | –CH₃ | S | new compound |

The following instant compounds having the appropriate substituents designated in Table 2D for Formula (I) above act in the same way as active compound (26), which has a pronouncedly selective-herbicidal action in wheat and carrots:

(7'') 3-ethylamino-4-amino-6-phenyl-1,2,4-triazine-5-one
(33') 3-methoxy-4-amino-6-phenyl-1,2,4-triazine-5-one.

The following Examples, by way of illustration and

Table 2D

| | R | $R_1$ | $R_2$ | $R_3$ | $R_4$ | Y | |
|---|---|---|---|---|---|---|---|
| (3') | phenyl | H | H | –C₂H₅ | | S | new compound |
| (17') | phenyl | | =C(CH₃)₂ | –CH₃ | | S | new compound |
| (18') | phenyl | | =⟨H⟩ (cyclohexylidene) | –CH₃ | | S | new compound |
| (35) | phenyl | | =CH–(furan-NO₂) | –CH₃ | | S | new compound |

EXAMPLE 3

Defoliant test

There is prepared, in the same manner as described in Example 1, an active compound preparation which contains 0.05% of
(1a'') 3-methylthio-4-amino-6-phenyl-1,2,4-triazine-5-one.

A field of dwarf beans is sprayed with this preparation of the active compound so that the dwarf beans themselves are only just dripping wet.

After 8 days the leaves are completely dried up.

not limitation, contain detailed particulars of various methods of preparation of different 1,3,4-triazine-5ones of the present invention. They exemplify methods which are in accordance with known types.

EXAMPLE 4

Preparation of 3-hydroxy-1,2,4-triazone-5-ones with different substituents in the 6-position:

74g carbohydrazide are heated to 90–100°C with 600 ml water. 74g pyroracemic acid are added dropwise, with stirring. After 3 hours, filtering off cold with suction is effected to yield:

(36) 3-hydroxy-4-amino-6-methyl-1,2,4-triazine-5-one, m.p. 159°C (from alcohol).

In analogous manner there are also obtained for instance:

(37) 3-hydroxy-4-amino-6-benzyl-1,2,4-triazine-5-one, m.p. 173°C

(38) 3-hydroxy-4-amino-6-phenyl-1,2,4-triazine-5-one, m.p. 195°C

EXAMPLE 5

Modification of 3-hydroxy-1,2,4-triazine-5-ones:

20.4g 3-hydroxy-4-amino-6-phenyl-1,2,4-triazine-5-one (38′) are dissolved in 300 ml dimethylformamide and 50 cc 2N sodium methylate solution. The excess methanol is then distilled off in a vacuum, and 13.5g β-diethylaminoethyl chloride are added dropwise at 80°C, with stirring, to the remaining dimethylformamide solution. After a short time the reaction mixture is neutral to phenolphthalein. The solvent is distilled off under reduced pressure. The residue is taken up in water and methylene chloride, and the organic phase is separated and fractionally distilled to yield:

(39) 3-(β-diethylaminoethoxy)-4-amino-6-phenyl-1,2,4-triazine-5-one, b.p. 160°C/0.01 mm Hg.

Substitution products of 3-hydroxy-1,2,4-triazin-5-ones, indirect method of preparation: 2.3 g sodium are added to 500 ml methanol whereby a sodium methylate solution is formed. 23.4g 3-methylthio-4-amino-6-phenyl-1,2,4-triazin-5-one and 6.5 ml methyl iodide are added. The mixture is boiled for one hour. When cooling down the mixture, a crystalline precipitate separates. The crystals are removed by suction and recrystallized from methanol and optionally once more from acetic acid ester. The 3-methoxy-4-amino-6-phenyl-1,2,4-triazin-5-one thus obtained has a melting point of 165°C.

In analogous manner there are also obtained for instance:

(40) 3-methoxy-4-amino-6-methyl-1,2,4-triazine-5-one, m.p. 124°C (33″) 3-methoxy-4-amino-6-phenyl-1,2,4-triazine-5-one, m.p. 167°C

(41) 3-ethoxy-4-amino-6-phenyl-1,2,4-triazine-5-one, m.p. 137°C

(42) 3-butoxy-4-amino-6-phenyl-1,2,4-triazine-5-one, m.p. 77°C

(43) 3-hexoxy-4-amino-6-phenyl-1,2,4-triazine-5-one, m.p. 77°C

(44) 3-allyloxy-4-amino-6-phenyl-1,2,4-triazine-5-one, m.p. 75°C

(45) 3-propargyloxy-4-amino-6-phenyl-1,2,4-triazine-5-one, m.p. 115°C

(46) 3-(3′,3′-dichlorallyloxy)-4-amino-6-phenyl-1,2,4-triazine-5-one, m.p. 84°C

(47) 3-(β-diethylaminoethoxy)-4-amino-6-methyl-1,2,4-triazine-5-one, b.p. 121°C/0.01 mm Hg.

(48) 3-(β-diethylaminoethoxy)-4-amino-6-benzyl-1,2,4-triazine-5-one, b.p. 165°C, 0.01 mm Hg.

EXAMPLE 6

Modification of 3-hydroxy-4-amino-1,2,4-triazine-5-ones:

10g 3-hydroxy-4-amino-6-methyl-1,2,4-triazine-5-one (36′) are boiled for 3 hours with 100 ml acetic anhydride. The excess acetic anhydride serving as solvent is distilled off in a vacuum and the residue is dissolved in, and allowed to crystallize (without filtration) from, alcohol to yield:

(49) 3-acetoxy-4-diacetylamino-6-methyl-1,2,4-triazine-5-one, m.p. 212°C.

EXAMPLE 7

Preparation of 3-mercapto-1,2,4-triazine-5-ones with different substituents in 6-position:

When 14g thiocarbohydrazide and 14g furoylformic acid are reacted according to Example 4, there is obtained

(50) 3-mercapto-4-amino-6-furyl-1,2,4-triazine-5-one, m.p. 244°C.

In analogous manner there can also be prepared for instance:

(51) 3-mercapto-4-amino-6-methyl-1,2,4-triazine-5-one, m.p. 180°C

(52) 3-mercapto-4-amino-6-benzyl-1,2,4-triazine-5-one, m.p. 205°C

(53) 3-mercapto-4-amino-6-phenyl-1,2,4-triazine-5-one, m.p. 242°C

(54) 3-mercapto-4-amino-6-isobutyl-1,2,4-triazine-5-one, m.p. 156°C

(55) 3-mercapto-4-amino-6-(4′-chlorophenyl)-1,2,4-triazine-5-one, m.p. 264°C

(56) 3-mercapto-4-amino-6-(4′-chlorbenzyl)-1,2,4-triazine-5-one, m.p. 224°C

(57) 3-mercapto-4-amino-6-ethyl-1,2,4-triazine-5-one, m.p. 123°C

(58) 3-mercapto-4-amino-6-isopropyl-1,2,4-triazine-5-one, m.p. 140°C

(59) 3-mercapto-4-amino-6-cyclohexyl-1,2,4-triazine-5-one, m.p. 166°C

(60) 3-mercapto-4-amino-6-isopentyl-1,2,4-triazine-5-one, m.p. 143°C

(61) 3-mercapto-4-amino-6-hexyl-1,2,4-triazine-5-one, m.p. 126°C

(62) 3-mercapto-4-amino-6-carbethoxy-methyl-1,2,4-triazine-5-one, m.p. 134°C

(63) 3-mercapto-4-amino-6-(4′-methyl-phenyl)-1,2,4-triazine-5-one, m.p. 222°C 64) 3-mercapto-4-amino-6-(3′-methyl-phenyl)-1,2,4-triazine-5-one, m.p. 214°C

(65) 3-mercapto-4-amino-6-(3′-methoxy-phenyl)-1,2,4-triazine-5-one, m.p. 200°C

(66) 3-mercapto-4-amino-6-(3′-chloro-phenyl)-1,2,4-triazine-5-one, m.p. 242°C

(67) 3-mercapto-4-amino-6-(4′-nitro-phenyl)-1,2,4-triazine-5-one, m.p. 222°C

(68) 3-mercapto-4-amino-6-benzylmercapto-methyl-1,2,4-triazine-5-one, m.p. 169°C

(69) 3-mercapto-4-methylamino-6-phenyl-1,2,4-triazine-5-one, m.p. 129°C

(70) 3-mercapto-4-amino-6-styryl-1,2,4-triazine-5-one, m.p. 258°C (decomp.)

EXAMPLE 8

Modification of 3-mercapto-1,2,4-triazine-5-ones:

When 38.7g 3-mercapto-4-amino-6-methyl-1,2,4-triazine-5-one (51′) are reacted according to Example 5 in dimethylformamide with sodium methylate and β-diethylamino-ethyl chloride, there is obtained

(71) 3-(β-diethylaminoethylthio)-4-amino-6-methyl-1,2,4-triazine-5-one, b.p. 141°C/0.01 mm Hg.

In analogous manner there are also obtained for instance:

(72) 3-(β-diethylaminoethylthio)-4-amino-6-phenyl-1,2,4-triazine-5-one as HCl salt, m.p. 220°C (29a″) 3-methylthio-4-amino-6-methyl-1,2,4-triazine-5-one, m.p. 166°C (4″) 3-methylthio-4-amino-6-benzyl-1,2,4-triazine-5-one, m.p. 205°C
(1a‴) 3-methylthio-4-amino-6-phenyl-1,2,4-triazine-5-one, m.p. 188°C
(30′) 3-methylthio-4-amino-6-(4′-chlorobenzyl)-1,2,4-triazine-5-one, m.p. 183°C
(73) 3-methylthio-4-amino-6-(4′-chlorphenyl)-1,2,4-triazine-5-one, m.p. 182°C
(5′) 3-methylthio-4-amino-6-furyl-1,2,4-triazine-5-one, m.p. 225°C
(74) 3-allylthio-4-amino-6-furyl-1,2,4-triazine-5-one, m.p. 165°C
(75) 3-propynylthio-4-amino-6-furyl-1,2,4-triazine-5-one, m.p. 174°C
(31′) 3-propynylthio-4-amino-6-phenyl-1,2,4-triazine-5-one, m.p. 159°C
(32′) 3-allylthio-4-amino-6-phenyl-1,2,4-triazine-5-one, m.p. 137°C
(76) 3-allylthio-4-amino-6-(4′-chlorbenzyl)-1,2,4-triazine-5-one, m.p. 157°C
(77) 3-isopropylthio-4-amino-6-phenyl-1,2,4-triazine-5-one, m.p. 150°C
(78) 3-dodecylthio-4-amino-6-phenyl-1,2,4-triazine-5-one, m.p. 103°C
(79) 3-benzylthio-4-amino-6-phenyl-1,2,4-triazine-5-one, m.p. 169°C
(80) 3-(4′-chlorbenzylthio)-4-amino-6-phenyl-1,2,4-triazine-5-one, m.p. 184°C
(81) 3-(4′-chlorbenzylthio)-4-amino-6-methyl-1,2,4-triazine-5-one, m.p. 186°C
(82) 3-isobutylthio-4-amino-6-methyl-1,2,4-triazine-5-one, m.p. 65°C
(3″) 3-ethylthio-4-amino-6-phenyl-1,2,4-triazine-5one, m.p. 114°C
(83) 3-propylthio-4-amino-6-phenyl-1,2,4-triazine-5-one, m.p. 119°C
(84) 3-butylthio-4-amino-6-phenyl-1,2,4-triazine-5-one, m.p. 100°C
(85) 3-hexylthio-4-amino-6-phenyl-1,2,4-triazine-5-one, m.p. 87°C
(86) 3-cyclohexylthio-4-amino-6-phenyl-1,2,4-triazine-5-one, m.p. 160°C
(87) 3-(2,3-dichlorallylthio)-4-amino-6-phenyl-1,2,4-triazine-5-one, m.p. 215°C
(88) 3-octadecylthio-4-amino-6-phenyl-1,2,4-triazine-5-one, m.p. 94°C
(22″) 3-methylthio-4-amino-6-ethyl-1,2,4-triazine-5-one, m.p. 120°C
(21′) 3-methylthio-4-amino-6-isopropyl-1,2,4-triazine-5-one, m.p. 123°C
(2″) 3-methylthio-4-amino-6-cyclohexyl-1,2,4-triazine-5-one, m.p. 154°C
(11″) 3-methylthio-4-amino-6-isobutyl-1,2,4-triazine-5-one, m.p. 66°C
(23″) 3-methylthio-4-amino-6-isopentyl-1,2,4-triazine-5-one, stiff oil
(24″) 3-methylthio-4-amino-6-n-hexyl-1,2,4-triazine-5-one, m.p. 63°C
(89) 3-methylthio-4-amino-6-styryl-1,2,4-triazine-5-one, m.p. 218°C
(90) 3-methylthio-4-amino-6-carbomethoxy-methyl-1,2,4-triazine-5-one, m.p. 112°C
(91) 3-methylthio-4-amino-6-(3′-methyl-phenyl)-1,2,4-triazine-5-one, m.p. 160°C
(92) 3-methylthio-4-amino-6-(4′-methyl-phenyl)-1,2,4-triazine-5-one, m.p. 185°C
(93) 3-methylthio-4-amino-6-(3′-chloro-phenyl)-1,2,4-triazine-5-one, m.p. 219°C
(94) 3-methylthio-4-amino-6-(3′-methoxy-phenyl)-1,2,4-triazine-5-one, m.p. 142°C
(95) 3-methylthio-4-amino-6-benzylmercapto-methyl-1,2,4-triazine-5-one, m.p. 110°C

EXAMPLE 9

Modification of 3-methylthio-1,2,4-triazine-5-ones:
11.7g 3-methylthio-4-amino-6-methyl-1,2,4-triazine-5-one (29a‴) and 15g p-chloraniline are stirred together with each other for 1 hour at 150°C and then 1 hour at 160°C. After this the melt has become solid. After cooling, the melt is boiled out with ether. The insoluble portion is dissolved in, and allowed to crystallize (without filtration) from, dimethylformamide. There is obtained
(96) 3-(4′-chlorophenylamino)-4-amino-6-methyl-1,2,4-triazine-5-one, m.p. 242°C.

When, instead of p-chloraniline, an amine is used with which, because of its volatility, the above-mentioned reaction temperatures cannot be achieved in an open vessel, the work is carried out in an autoclave.

The following compounds for instance can also be prepared in this manner:
(97) 3-(3′,4′-dichlorophenylamino)-4-amino-6-methyl-1,2,4-triazine-5-one, m.p. 228°C
(98) 3-(2′,4′-dichlorphenylamino)-4-amino-6-methyl-1,2,4-triazine-5-one, m.p. 218°C
(99) 3-(β-diethylaminoethylamino)-4-amino-6-methyl-1,2,4-triazine-5-one, m.p. 108°C
(34′) 3-methylamino-4-amino-6-methyl-1,2,4-triazine-5-one, m.p. 180°C
(7‴) 3-ethylamino-4-amino-6-phenyl-1,2,4-triazine-5-one, m.p. 158°C
(9′) 3-methylamino-4-amino-6-phenyl-1,2,4-triazine-5-one, m.p. 212°C
(100) 3-n-butylamino-4-amino-6-phenyl-1,2,4-triazine-5-one, m.p. 182°C
(12′) 3-n-propylamino-4-amino-6-phenyl-1,2,4-triazine-5-one, m.p. 176°C
(13a″) 3-morpholino-4-amino-6-phenyl-1,2,4-triazine-5-one, m.p. 163°C
(101) 3-(β-diethylaminoethylamino)-4-amino-6-phenyl-1,2,4-triazine-5-one, m.p. 130°C
(102) 3-benzylamino-4-amino-6-phenyl-1,2,4-triazine-5-one, m.p. 177°C
(103) 3-(4′-chloranilino)-4-amino-6-phenyl-1,2,4-triazine-5-one, m.p. 257°C
(104) 3-(4′-chloranilino)-4-amino-6-(4′clorbenzyl)-1,2,4-triazine-5-one, m.p. 212°C
(105) 3-(β-diethylaminoethylamino)-4-amino-6-(4′-chlorbenzyl)-1,2,4-triazine-5-one, m.p. 148°C
(10″) 3-methylamino-4-amino-6-(4′-chlorbenzyl)-1,2,4-triazine-5-one, m.p. 159°C
(106) 3-benzylamino-4-amino-6-(4′-chlorbenzyl)-1,2,4-triazine-5-one, m.p. 123°C
(107) 3-(β-diethylaminoethylamino)-4-amino-6-(4′-chlorphenyl)-1,2,4-triazine-5-one, m.p. 184°C
(25′) 3-piperidino-4-amino-6-phenyl-1,2,4-triazine-5-one, m.p. 149°C
(26″) 3-allylamino-4-amino-6-phenyl-1,2,4-triazine-5-one, m.p. 168°C
(108) 3-octadecylamino-4-amino-6-phenyl-1,2,4-triazine-5-one, m.p. 129°C
(109) 3-n-hexylamino-4-amino-6-phenyl-1,2,4-triazine-5-one, m.p. 164°C
(110) 3-[2′-(ethyl)-hexylamino]-4-amino-6-phenyl-1,2,4-triazine-5-one, m.p. 131°C (111) 3-diethylamino-4-amino-6-phenyl-1,2,4-triazine-5-one, m.p. 133°C

EXAMPLE 10

Preparation of 3,4-diamino-1,2,4-triazine-5-ones:

43g 1,3-diamino-guanidine-hydrobromide are dissolved in a little water; 38g benzoylformic acid, dissolved in methanol, are added. After brief heating, cooling is effected followed by neutralization with bicarbonate. There is obtained in this way (112) 3,4-diamino-6-phenyl-1,2,4-triazine-5-one, m.p. 258°C.

In analogous manner, with p-chlorbenzoylformic acid there is prepared (113) 3,4-diamino-6-(4'-chlorphenyl)-1,2,4-triazine-5-one, m.p. 255°C.

EXAMPLE 11

Preparation of 3-methylthio-4-acetylamino-6-phenyl-1,2,4-triazine-5-one:

20g 3-methylthio-4-amino-6-phenyl-1,2,4-triazine-5-one (1a'''') are boiled for 9 hours with 100 cc acetic anhydride. The excess anhydride is then distilled off under reduced pressure. The crystalline residue is dissolved in, and allowed to crystallize (without filtration) from, alcohol to yield:

(6') 3-methylthio-4-diacetylamino-6-phenyl-1,2,4-triazine-5-one, m.p. 122°C 20g of this last mentioned compound are dissolved in alcohol and treated at 20°C with an equivalent of 2N sodium hydroxide solution, which is consumed very rapidly. After working up, there is obtained (8') 3-methylthio-4-acetylamino-6-phenyl-1,2,4-triazine-5-one, m.p. 213°C.

EXAMPLE 12

Modification of 3-methylthio-4-amino-1,2,4-triazine-5-ones at the amino group:

23.4g 3-methylthio-4-amino-6-phenyl-1,2,4-triazine-5-one (1a''''') are dissolved in 100 ml chlorobenzene with 17.8g freshly distilled chloral and 0.2g p-toluenesulfonic acid. The reaction mixture is heated for 1 hour on a water-bath and then for 45 minutes under reflux. A small amount of undissolved matter is filtered off hot. From the filtrate there crystallizes (20'') 3-methylthio-4-($\beta$-trichloro-$\alpha$-hydroxy-ethyl)-amino-6-phenyl-1,2,4-triazine-5-one.

After dissolving in, and allowing to crystallize (without filtration) from, chloroform, such product has: m.p. 147°C (decomp.).

11.7g 3-methylthio-4-amino-6-phenyl-1,2,4-triazine-5-one (1a''''') and 5.6g cyclohexanone are boiled for 1 hour in 50 ml methanol after the addition of 5 drops of concentrated hydrochloric acid. The crystals which have precipitated during cooling are dissolved in, and allowed to recrystallize (without filtration) from, methanol to yield:

(18'') 3-methylthio-4-cyclohexylidene-amino-6-phenyl-1,2,4-triazine-5-one, m.p. 140°C.

In analogous manner, there are also obtained for instance:

(15'') 3-methylthio-4-benzylidene-amino-6-phenyl-1,2,4-triazine-5-one, m.p. 180°C (14'') 3-methylthio-4-(furfurylidene-2'-)amino-6-phenyl-1,2,4-triazine-5-one, m.p. 172°C (35') 3-methylthio-4-(5'-nitrofurfurylidene-2'-)-amino-6-phenyl-1,2,4-triazine-5-one, m.p. 207°C (17'') 3-methylthio-4-(2'-propylidene-amino)-6-phenyl-1,2,4-triazine-5-one, m.p. 152°C (19'') 3-methylthio-4-(isobutylidene-amino)-6-phenyl-1,2,4-triazine-5-one, m.p. 136°C (27'') 3-methylthio-4-(1'-phenyl-ethylidene-amino)-6-phenyl-1,2,4-triazine-5-one, m.p. 154°C (28'') 3-methylthio-4-[pyridyl-(2-methylidene-amino]-6-phenyl-1,2,4-triazine-5-one, m.p. 205°C

EXAMPLE 13

In the same manner as described in Example 4, using corresponding molar amounts of the appropriate starting materials, the following compounds are produced:

(114) 3-naphthyl-n-propyloxy-4-isooctylamino-6-hexadec-1-yl-1,2,4-triazine-5-one (115) 3-phenyl-tert-butyloxy-4-formylamino-6-vinyl-1,2,4-triazine-5-one (116) 3-naphthyloxy-4-butanoylamino-6-dodec-11-en-1-yl-1,2,4-triazine-5-one (117) 3-cyclopent-3-enyloxy-4-(2-cyano-2-methyl-ethylamino)-6-prop-2-yn-1-yl-1,2,4-triazine-5-one (118) 3-(3-nitro-5-bromo-6-fluoro-hept-5-yn-1-yloxy)-4-(2-bromo-2-fluoro-acetylamino)-6-octadec-9-yn-1-yl-1,2,4-triazine-5-one (119) 3-(3-iodo-5-fluoro-cyclohexyloxy)-4-hexylidene-amino-6-naphthylmethyl-1,2,4-triazine-5-one (120) 3-(3-methoxy -4-sec-butyl-5-chloro-phenylethyloxy)-4-cyclopentylidene-amino-6-naphthylisopropyl-1,2,4-triazine-5-one (121) 3-(4-phenoxynaphthyloxy)-4-(3phenyl-n-propylideneamino)-6-naphthyl-n-but-2-enyl-1,2,4-triazine-5-one (122) 3-naphthylethylmercapto-4-[5-(3-chloro-4-bromo-5-iodo-phenyl) pentylidene-amino]-6-naphthyl-1,2,4-triazine-5-one (123) 3-phenyl-isopropylmercapto-4-[2-(4-n-butoxyphenyl) ethylidene-amino]-6-tetrahydrofuryl-1,2,4-triazine-5-one (124) 3-naphthylmercapto-4-[4-(4-nitronaphthyl) cyclohexylidene-amino]-6-piperidyl-1,2,4-triazine-5-one (125) 3-cyclohex-3-enylmercapto-4-piperidyl-6-morpholino-1,2,4-triazine-5-one (126) 3-(5-chloro-5-bromo-10-nitro-dec-9-en-1-ylmercapto)-4-thiazolo-6-thienyl-1,2,4-triazine-5-one (127) 3-(3-ethoxy-5-isopropyl-naphthyl-n-propylmercapto)-4-(4-pyrano cyclopentylideneamino)-6-(10-bromodec-1-yl)-1,2,4-triazine-5-one (128) 3-(3-naphthyloxy phenylmercapto)-4-pyrazolo-6-(3-iodo-4-fluoro-cyclopent-2-enyl)-1,2,4-triazine-5-one (129) 3-(phenylethylamino)-4-dioxazolo-6-(3-isopropylmercaptoallyl)-1,2,4-triazine-5-one (130) 3-[N-(2-nitro-3-iodo-4-chloro-5-ethyl-phenyl)-N-cyclohexyl-amino]-4-pyrimidino-6-(4-phenyloxy pyridyl)-1,2,4-triazine-5-one (131) 3-[N-(3-n-propoxy-4-phenyloxy-cyclohexyl)-N-isohexyl-amino]-4-pyrrolo-6-(4-phenylmercapto-n-but-3-ynyl)-1,2,4-triazine-5-one (132) 3-(4-naphthyloxy phenyl-amino)-4-pyrrodiazolo-6-(3-naphthylmercapto-4-acetyloxy-furyl)-1,2,4-triazine-5-one (133) 3-(thiazolino)-4-thiodiazolo-6-(3-chloro-4-nitro-5-ethoxy-phenyl-n-propyl)-1,2,4-triazine-5-one Advantageously, in accordance with the present invention, in the foregoing formulae, as the case may be:

R represents (i) aliphatic hydrocarbon having 1–18 carbon atoms, including methyl, ethyl, n-propyl, isopropyl, n-butyl, isobutyl, sec-butyl, tert-butyl, amyl, isoamyl, hexyl, isohexyl, heptyl, octyl, isooctyl, nonyl, decyl, undecyl, dodecyl, tridecyl, tetradecyl, pentadecyl, hexadecyl, heptadecyl, octadecyl, and the like, especially alkyl having 1–18 carbon atoms, preferably 1–6 carbon atoms, more especially lower alkyl, and most especially alkyl having 1–4 carbon atoms, further including vinyl, α-, β- and γ-allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, and the like, especially alkenyl having 2–18 carbon atoms, preferably 2–6 carbon atoms, more especially lower alkenyl, and most especially alkenyl having 2–4 carbon atoms; and still further including acetylenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, and the like, especially alkynyl having 2–18 carbon atoms, preferably 2–6 carbon atoms, more especially lower alkynyl, and most especially alkynyl having 2–4 carbon atoms;

(ii) cycloaliphatic hydrocarbon having 5–8 ring carbon atoms, including cyclopentyl, cyclohexyl, cycloheptyl, cyclooctyl, cyclopentenyl, cyclohexenyl, cycloheptenyl, cyclooctenyl, cyclopenynyl, cyclohexynyl, cyclooctynyl, and the like, especially cycloalkyl having 5–8 carbon atoms, and most especially cycloalkyl having 5–6 carbon atoms;

(iii) araliphatic hydrocarbon having 6–10 ring carbon atoms and 1–4 aliphatic carbon atoms, including phenyl- and naphthyl-methyl, ethyl, n-propyl, isopropyl, n-butyl, isobutyl, sec-butyl, tert-butyl, vinyl, allyl, butenyl, acetylenyl, propynyl, butynyl, and the like, especially mono- and di-nuclear $C_{6-10}$ aryl substituted $C_{1-4}$ aliphatic, and most especially phenyl- and naphthyl-substituted $C_{1-4}$ alkyl, $C_{2-4}$ alkenyl, and $C_{2-4}$ alkynyl;

(iv) aryl hydrocarbon having 6–10 ring carbon atoms, including phenyl, naphthyl, and the like, especially mono- and di-nuclear $C_{6-10}$ aryl;

(v) heterocyclic having 5–6 ring members including at least one hetero linking atom such as oxygen, nitrogen, and/or sulfur, such as furyl, di- and tetra-hydrofuryl, dioxano, pyrano, dioxino, dioxazolo, morpholino, thioxano, pyrazolo, pyrrolino, pyrrolidino, piperidyl, pyridyl, pyrazolo, pyrazolino, pyrazolidino, pyridazino, pyrimidino, pyrrodiazolo, thiopheno (especially thienyl), thiophano, thiazolo, thiazolino, thiazolidino, thiazino, thiodiazino, thiodiazolo, and the like, and especially furyl, pyridyl and thienyl; as well as (vi) all of such aliphatic, cycloaliphatic, araliphatic, aryl and heterocyclic set forth under (i), (ii), (iii), (iv) and (v) above which are mono, di, poly and mixed substituted with substituents including halo, such as chloro, bromo, iodo and fluoro; nitro, carboloweralkoxy such as carbo-(methyl to tert-butyl inclusive, and the like, as noted above) -oxy, especially carboalkoxy having 1–6, and preferably 1–5, carbon atoms, and most especially carboalkoxy having 1–4 carbon atoms in the alkoxy moiety; lower alkyl such as methyl to tert-butyl inclusive as noted above, especially $C_{1-4}$ alkyl; lower alkoxy such as methoxy, ethoxy, n-propoxy, isopropoxy, n-butoxy, isobutoxy, sec-butoxy, tert-butoxy, and the like, especially $C_{1-4}$ alkoxy; aryl lower alkylmercapto such as mono- and di-nuclear $C_{6-10}$ aryl substituted lower alkyl mercapto, especially $C_{6-10}$ aryl-$C_{1-4}$ alkylmercapto, and particularly phenyl- and naphthyl- (methyl to tert-butyl inclusive, and the like, as noted above) mercapto; lower alkyl mercapto such as (methyl to tert-butyl inclusive, and the like, as noted above) mercapto, and especially $C_{1-4}$ alkyl mercapto; $C_{6-10}$ aryl mercapto such as phenyl- and naphthyl-mercapto, and the like, especially mono- and di-nuclear arylmercapto having 6–10 ring carbon atoms; $C_{6-10}$ aryloxy such as phenoxy, naphthyloxy, and the like, especially mono- and di-nuclear aryloxy having 6–10 ring carbon atoms;

$R_1$ and $R_2$ each respectively represents (vii) hydrogen;

(viii) alkyl having 1–12 carbon atoms such as methyl to dodecyl inclusive, and the like, as noted above, especially lower alkyl, and most especially $C_{1-4}$ alkyl;

(ix) alkanoyl having 1–6 carbon atoms such as formyl, acetyl, propionyl, butyryl, pentanoyl, hexanoyl, and the like, especially $C_{1-5}$, preferably $C_{1-4}$, alkyl carbonyl; as well as (x) all such alkyl and alkanoyl set forth under (viii) and (ix) above which are mono, di, poly and mixed substituted with substituents including cyano, hydroxy and halo such as chloro, bromo, iodo and/or fluoro;

with the proviso that $R_1$ and $R_2$ when taken together represents (xi) alkylidene hydrocarbon having 1–6 carbon atoms including methylidene, ethylidene, n-propylidene, isopropylidene, n-butylidene, isobutylidene, sec-butylidene, pentylidene, hexylidene, and the like, especially lower alkylidene, and more especially $C_{1-4}$ alkylidene;

(xii) cycloalkylidene hydrocarbon having 5–8 ring carbon atoms including cyclopentylidene, cyclohexylidene, cycloheptylidene, cyclooctylidene, and the like, especially cycloloweralkylidene and more especially cyclo $C_{5-6}$ alkylidene; as well as (xiii) all such alkylidene and cycloalkylidene set forth under (xi) and (xii) above which are mono, di, poly and mixed substituted with substituents including aryl having 6–10 ring carbon atoms, including phenyl, naphthyl, and the like, especially mono- and di-nuclear $C_{6-10}$ aryl; haloaryl having 6–10 ring carbon atoms, including halo, i.e., chloro, bromo, iodo and/or fluoro, -phenyl, -naphthyl, and the like, especially mono- and di-nuclear halo $C_{6-10}$ aryl; nitroaryl having 6–10 ring carbon atoms, including nitrophenyl, nitronaphthyl, and the like, especially mono- and di-nuclear nitro $C_{6-10}$ aryl; lower alkoxy aryl having 6–10 ring carbon atoms including methoxy to tert-butoxy inclusive, and the like, substituted -phenyl, -naphthyl, and the like, especially mono- and di-nuclear $C_{1-4}$ alkoxy $C_{6-10}$ aryl; and heterocyclic having 5–6 ring members including at least one hetero linking atom as set forth under (v) above and particularly furyl, nitrofuryl and pyridyl;

Y represents oxygen, sulfur or

and $R_3$ and $R_4$, as the case may be, each respectively represents (xiv) hydrogen;

(xv) aliphatic hydrocarbon having 1–18 carbon atoms as set forth under (i) above;

(xvi) cycloaliphatic hydrocarbon having 5–8 ring carbon atoms as set forth under (ii) above;

(xvii) araliphatic hydrocarbon having 6–10 ring carbon atoms and 1–4 aliphatic carbon atoms as set forth under (iii) above;

(xviii) aryl hydrocarbon having 6–10 ring carbon atoms as set forth under (vi) above; as well as (xix) all such aliphatic, cycloaliphatic, araliphatic, and aryl set forth under (xv), (xvi), (xvii) and (xviii) above which are mono, di, poly and mixed substituted with substituents including halo, such as chloro, bromo, iodo and fluoro; amino, including unsubstituted amino and lower alkyl substituted amino such as N-lower alkyl and N,N-dilower alkyl amino, especially having 1–4 carbon atoms in each corresponding alkyl moiety, and particularly methyl to tert-butyl inclusive as noted above; nitro; lower alkyl such as methyl to tert-butyl inclusive as noted above, and especially $C_{1-4}$ alkyl; lower alkoxy such as methoxy to tert-butoxy inclusive as noted above, and especially $C_{1-4}$ alkoxy; and aryloxy having 6–10 ring carbon atoms such as phenoxy, naphthyloxy, and the like, especially mono- and di-nuclear $C_{6-10}$ aryloxy;

with the proviso that $R_3$ and $R_4$ when taken together with the adjacent nitrogen atom represent heterocyclic having 5–6 ring members including at least one hetero linking atom as set forth under (v) above, and particularly morpholino and piperidyl; and with the further proviso that when Y is oxygen $R_3$ may also be lower alkanoyl such as formyl, acetyl, propionyl, butyryl, pentanoyl, and the like, and especially alkanoyl having 1–5, preferably 1–4, carbon atoms.

With specific reference to the particular new compounds of the present invention:

(a) when Y is 0,

R, $R_1$, $R_2$ and $R_3$ are the same as defined under (i) through (xix) above, respectively, as the case may be, with the proviso that $R_3$ may also be lower alkanoyl such as formyl, acetyl, propionyl, butyryl, pentanoyl, and the like, and especially alkanoyl having 1–5, preferably 1–4, carbon atoms;

(b) when Y is S, and $R_1$, $R_2$ and $R_3$ are the same as defined under (a) above, R is the same as defined under (a) above, with the proviso that when R is aliphatic in accordance with (i) above, said aliphatic always has at least 2, or at least 3, or at least 4, or at least 5, or at least 6, or more, and up to 18 carbon atoms and preferably has 2–6, 3–6, 4–6, or 5–6 carbon atoms, and with the further proviso that when R is aryl in accordance with (iv) above, such aryl is always substituted aryl which is substituted in accordance with (vi) above;

(c) when Y is S, and R, $R_1$ and $R_2$ are the same as defined under (a) above, $R_3$ is the same as defined under (xv) through (xix) above, respectively, with the proviso that when $R_3$ is aliphatic in accordance with (xv) above, such aliphatic always has at least 2, or at least 3, or at least 4, or at least 5, or at least 6, or more and up to 18 carbon atoms, and preferably has 2–6, 3–6, 4–6, or 5–6 carbon atoms;

(d) when Y is S, and R and $R_3$ are the same as defined under (a) above, $R_1$ and $R_2$ each respectively is the same as defined under (viii) and (x) above, as the case may be, with the proviso that $R_1$ and $R_2$ when taken together represent alkylidene or cycloalkylidene as defined under (xi) through (xiii) above, with the proviso that such alkylidene when substituted with aryl having 6–10 carbon atoms always has at least 2, or at least 3, or at least 4, or at least 5, or at least 6, or more and up to 18 carbon atoms, and preferably has 2–6, 3–6, 4–6, or 5–6 carbon atoms;

(e) when Y is

and $R_1$, $R_2$ and $R_3$ are the same as defined under (a) above,

R is the same as defined under (b) above, and $R_4$ is defined individually in the same way as $R_3$ is defined wherein $R_3$ and $R_4$ may be alike or different, with the proviso that $R_3$ and $R_4$ when taken together with the adjacent nitrogen atom represent heterocyclic as defined under (v) above;

(f) when Y is

and R and $R_3$ are the same as defined under (a) above, $R_1$ and $R_2$ each respectively is the same as defined under (viii) through (xi) and (xiii) above, as the case may be, and $R_4$ is the same as defined under (e), with the proviso that $R_3$ and $R_4$ when taken together with the adjacent nitrogen atom represent heterocyclic as defined under (v) above; and (g) when Y is

and R, $R_1$ and $R_2$ are the same as defined under (a) above;

$R_3$ and $R_4$ each respectively is the same as defined under (xv), (xvi), (xviii) and (xix) above, as the case may be, with the proviso that $R_4$ may also be hydrogen and that when $R_4$ is hydrogen $R_3$ is aliphatic as defined under (i) above but having always only 1–3 carbon atoms, or cycloaliphatic as defined under (ii) above, or substituted-aliphatic having 1–18 carbon atoms, -cycloaliphatic or -aryl as defined under (i), (ii), (iv) and (xix), as the case may be, and with the further proviso that $R_3$ and $R_4$ when taken together with the adjacent nitrogen atom represent heterocyclic as defined under (v) above but always excluding oxygen as hetero atom.

All of the foregoing compounds contemplated by the present invention possess the desired selective herbicidal properties, and especially the capability of selectively destroying weeds. It will be realized that the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention which is to be limited only by the scope of the appended claims.

What is claimed is:

1. Herbicidal composition which comprises a mixture of an inert carrier vehicle selected from the group consisting of (1) a solid and (2) a dispersible liquid containing a surface active agent, and a herbicidally effective amount constituting substantially between about 0.001 and 95% by weight of the mixture of a 3-methylthio-4-amino-6-branched butyl-1,2,4-triazine-5-one having the formula

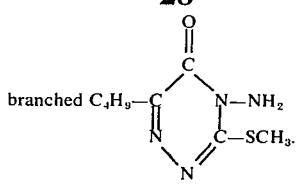

2. A composition according to claim 1 wherein branched butyl is tert-butyl.

3. A method for selectively controlling weeds in growing beans and potatoes which comprises applying to the locus thereof a herbicidally effective amount of a 3-methylthio-4-amino-6-branched butyl-1,2,4-triazine-5-one having the formula

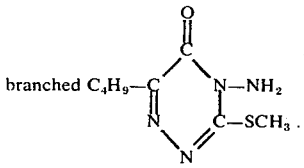

4. A method according to claim 3 wherein branched butyl is tert-butyl.

* * * * *